United States Patent [19]

Seiler

[11] 4,308,266

[45] Dec. 29, 1981

[54] 1,2,3,4-TETRAHYDRO-2-PIPERAZINYL-NAPHTHALENES FOR TREATING HYPERTENSION

[75] Inventor: Max-Peter Seiler, Basel, Switzerland

[73] Assignee: Sandoz Ltd., Basel, Switzerland

[21] Appl. No.: 73,943

[22] Filed: Sep. 7, 1979

Related U.S. Application Data

[63] Continuation of Ser. No. 925,493, Jul. 17, 1978, abandoned.

[30] Foreign Application Priority Data

Jul. 18, 1977 [CH] Switzerland .................. 8863/77
Nov. 8, 1977 [CH] Switzerland .................. 13583/77

[51] Int. Cl.$^3$ ............... A61K 31/42; A61K 31/50; C07D 295/08; C07D 233/50
[52] U.S. Cl. ................. 424/246; 424/248.4; 424/250; 424/251; 544/55; 544/96; 544/294; 544/360; 544/369; 544/370; 544/392; 544/394
[58] Field of Search ............ 544/392, 394, 55, 96, 544/294, 360, 369, 370; 424/246, 248.4, 250, 251

[56] References Cited

U.S. PATENT DOCUMENTS 4,018,773  4/1977  Condon et al. ............... 424/250
4,081,444  3/1978  Condon et al. ............... 424/250

Primary Examiner—Anton H. Sutto
Attorney, Agent, or Firm—Gerald D. Sharkin; Robert S. Honor; Thomas O. McGovern

[57] ABSTRACT

The present invention provides tetraline derivatives, useful for the treatment of hypertension, a process for their preparation and compositions containing these compounds.

43 Claims, No Drawings

1,2,3,4-TETRAHYDRO-2-PIPERAZINYL-NAPHTHALENES FOR TREATING HYPERTENSION

This is a continuation, of application Ser. No. 925,493 filed July 17, 1978, now abandoned.

This invention relates to tetraline derivatives. More particularly, the present invention provides compounds of formula I,

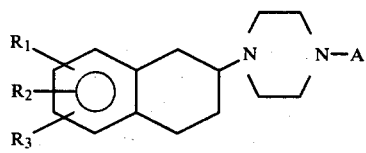

wherein $R_1$ is hydroxy, alkoxy of 1 to 4 carbon atoms, alkanoyloxy of 1 to 20 carbon atoms or a

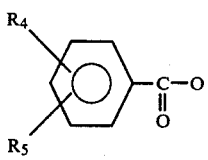

group,
wherein $R_4$ and $R_5$ may independently be hydrogen, fluorine, chlorine, bromine, iodine, alkyl of 1 to 4 carbon atoms or alkoxy of 1 to 4 carbon atoms or, when bonded to adjacent carbon atoms, $R_4$ and $R_5$ together may be a methylenedioxy group, $R_2$ and $R_3$ may independently be hydrogen, hydroxy, alkoxy of 1 to 4 carbon atoms, alkanoyloxy of 1 to 20 carbon atoms or a

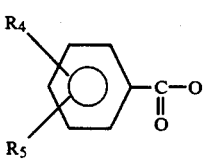

group, or when bonded to adjacent carbon atoms $R_1$ and $R_2$ together may be a methylenedixy group, A is
(a) a

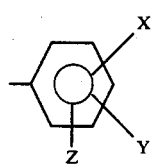

group,
wherin X, Y and Z may independently be hydrogen, hydroxy, alkyl of 1 to 4 carbon atoms, alkoxy of 1 to 4 carbon atoms, alkanoyloxy of 1 to 20 carbon atoms,
a

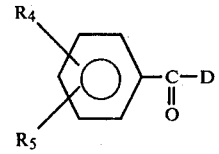

group, fluorine chlorine, bromine, iodine, $CF_3$, SH, alkylthio of 1 to 4 carbon atoms or alkanoylthio of 1 to 20 carbon atoms, or when bonded to adjacent carbon atoms X and Y together may be methylenedioxy, D is O or S
(b) a

group,
(c) a five or six membered ring of formula

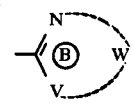

wherein
V is either divalent and signifies O, S, NH or $CH_2$ is trivalent and signifies N or CH,
W is a saturated or unsaturated alkylene chain of 2 or 3 carbon atoms
and ring B can contain 1, 2 or 3 double bonds.

The compounds of formula I can exist in the form of enantiomers or in racemate form.

In the aforementioned compounds all alkyl, alkoxy and alkanoyl groups which possess 3 or more carbon atoms, can be linear or branched.

$R_1$ is preferably hydroxy or alkoxy of 1 to 4 carbon atoms, especially hydroxy. When $R_1$ is alkoxy this is preferably methoxy. When $R_1$ is alkanoyloxy of 1 to 20 carbon atoms this may, for example, be of 15 to 20 carbon atoms or of 10 to 14 carbon atoms. Alternatively, $R_1$ may be alkanoyl of 1 to 4 carbon atoms or of 5 to 9 carbon atoms. $R_1$ is preferably in position 6- of the tetraline ring system.

Each of $R_4$ and $R_5$ may independently be hydrogen, fluorine, chlorine, bromine or iodine. Additionally, each of $R_4$ and $R_5$ may independently be alkyl of 1 to 4 carbon atoms or alkoxy of 1 to 4 carbon atoms. When $R_4$ and $R_5$ are bonded to adjacent carbon they may, together, be a methylenedioxy group. $R_2$ and $R_3$ are preferably hydrogen or hydroxy, especially hydrogen. When each of $R_2$ and $R_3$ independently signifies alkoxy of 1 to 4 carbon atoms, this is preferably methoxy. Each of $R_2$ and $R_3$ may independently signify alkanoyl of 1 to 20 carbon atoms, for example of 15 to 20 carbon atoms or of 10 to 14 carbon atoms. $R_2$ and $R_3$ may also independently signify alkanoyl of 1 to 4 carbon atoms or of 5 to 9 carbon atoms. When $R_2$ and $R_3$ independently signify a

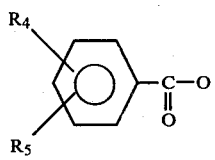

group, $R_4$ and $R_5$ may independently take any of the aforementioned significances.

When $R_1$ and $R_2$ are bonded to adjacent carbon atoms, they may, together, be a methylenedioxy group.

When X, Y and Z independently signify alkyl of 1 to 4 carbon atoms or alkoxy of 1 to 4 carbon atoms these are preferably methyl and methoxy. X is preferably alkyl of 1 to 4 carbon atoms. X and Y are preferably independently hydrogen, alkyl or alkoxy of 1 to 4 carbon atoms. X is preferably in position -2 of the phenyl residue. When X, Y and Z independently signify alkanoyl of 1 to 20 carbon atoms this may be alkanoyl of 15 to 20 carbon atoms or alkanoyl of 10 to 14 carbon atoms. X, Y and Z may also independently signify alkanoyl of 1 to 4 carbon atoms or alkanoyl of 5 to 9 carbon atoms. X, Y and Z may independently signify a

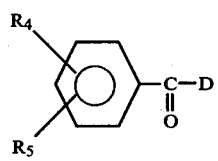

group, wherein D is oxygen or sulphur. X, Y and Z may also independently signify F, Cl, Br or I. Additionally each of X, Y and Z may be $CF_3$. In another group of compounds each of X, Y and Z may be SH. X, Y and Z may also be independently alkylthio of 1 to 4 carbon atoms. When X, Y and Z independently signify alkanoylthio of 1 to 20 carbon atoms this may, for example, be of 15 to 20 carbon atoms or of 10 to 14 carbon atoms. Additionally, X, Y and Z may independently be alkanoylthio of 1 to 4 carbon atoms or alkanoylthio of 5 to 9 carbon atoms. When bonded to adjacent carbon atoms X and Y may, together, be a methylenedioxy group.

A is preferably one of the moieties hereinbefore defined under (a).

A can also be a

group. When A is as hereinbefore defined under (c), the ring may be five or six membered. When V is divalent, this may be O, S, NH or $CH_2$. When V is trivalent, this may be N or CH. W can be a saturated or unsaturated alkylene chain of 2 or 3 carbon atoms. The ring Ⓑ can contain one, two or three double bonds.

The substituents $R_4$ and $R_5$ in the residues $R_1$, $R_2$, $R_3$, X, Y and Z can independently be any of their aforementioned significances.

The invention further provides a process for the production of a compound of formula I comprising, (a) producing a compound of formula Ia,

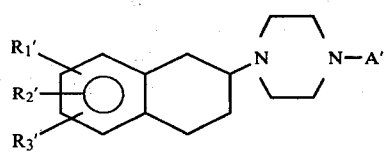

wherein
  $R_1'$ is alkoxy of 1 to 4 carbon atoms,
  $R_2'$ and $R_3'$ are independently hydrogen or alkoxy of 1 to 4 carbon atoms, or
  $R_1'$ and $R_2'$, when bonded to adjacent carbon atoms may be a methylenedioxy group, and
  A' has the same significances as A other than a phenyl residue substituted by at least one of the groups alkanoyloxy, alkanoylthio or

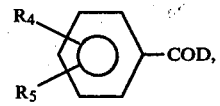

by reducing a compound of formula II,

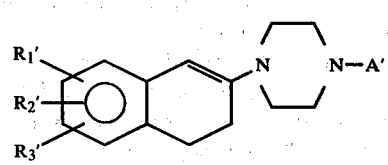

(b) producing a compound of formula Ib,

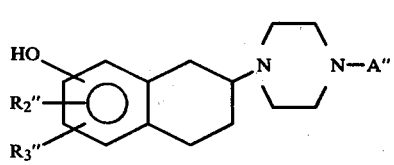

wherein each of $R_2''$ and $R_3''$ is independently hydrogen or hydroxy and
  A'' is a

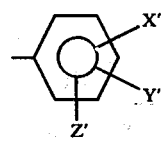

group,
  wherein each of X', Y' and Z' is independently hydrogen, hydroxy, alkyl of 1 to 4 carbon atoms, fluorine, chlorine, bromine, iodine, $CF_3$ or SH or for a moiety as previously defined under (b) and (c), by subjecting a compound of formula Ia to an ether cleavage reaction, (c) producing a compound of formula Ic,

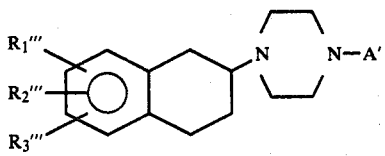

wherein $R_1'''$ is hydroxy or alkoxy of 1 to 4 carbon atoms and
each of $R_2'''$ and $R_3'''$ is independently hydrogen, hydroxy or alkoxy of 1 to 4 carbon atoms,
by condensing a compound of formula III,

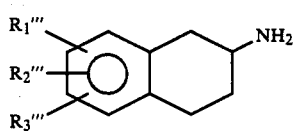

with a compound of formula IV,

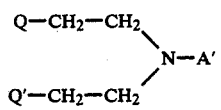

or (d) producing a compound of formula I wherein at least one of the substituents $R_1$, $R_2$, $R_3$, X, Y and Z is an alkanoyloxy or a

COO group,
and/or one of the substituents X, Y and Z is an alkanoylthio or

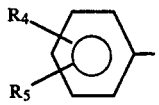

COS group,
by acylating a compound of formula I, wherin at least one of the substituents $R_1$, $R_2$, $R_3$, X, Y and Z is a free hydroxy group and/or one of the substituents X, Y and Z is a free SH group,
with a reactive derivative of an alkyl carboxylic acid of 1 to 20 carbon atoms or an aromatic carboxylic acid of formula

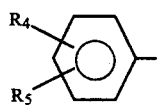

COOH.

Process variant (a) can be effected in known manner, for example by catalytic hydrogenation. Suitable catalysts include palladium/charcoal, platinum or Raney nickel, especially palladium/charcoal. The reaction may conveniently be effected in an inert organic solvent such as ethanol or dimethylformamide. The reduction can also be effected with complex metal hydrides, for example sodium borohydride, in an organic solvent such as trifluoroacetic acid. The reaction may conveniently be effected at a temperature of from 10° to 15° C., preferably from 20° to 30° C.

Process variant (b) can be effected according to known methods for ether cleavage reactions. The reaction is suitably effected in the presence of a cleaving agent such as hydriodic acid, hydrobromic acid or hydrochloric acid, advantageously in water or acetic acid, suitably at a temperature of from 0° to 100° C.; or boron tribromide, advantageously in methylene chloride, suitably at a temperature of from 0° to 50° C. With hydrogen chloride, the reaction is suitably effected at a pressure of from 1 to 10 atm. When X, Y or Z are alkoxy groups in the 2- or 6- position of the phenyl ring, these groups remain, for the most part unchanged and are not converted to free hydroxy groups.

Process variant (c) can be effected in known manner for the condensation of piperazine rings. Advantageously, the compounds of formula III and IV are heated to a temperature of from 60° to 120° C. in an inert organic solvent. Suitable organic solvents include ethanol, dimethylformamide or higher alcohols. The condensation can be effected in the presence of a base such as a tertiary amine or an alkali metal carbonate.

The residues Q and Q' are preferably chlorine, bromine, iodine an alkylsulphonyloxy or an arylsulphonyloxy group.

Process variant (d) can be effected in known manner for the acylation of phenols. Acid halides or anhydrides can, for example, be employed as reactive derivatives of a carboxylic acid.

The resulting compounds of formula I may be isolated and purified using conventional techniques. Where required, free base forms thereof may be converted into acid addition salt forms in conventional manner and vice versa. Suitable acids for salt formation include inorganic acids such as hydrochloric acid and organic acids such as maleic acid.

The optically active compounds of formula I can, for example, be prepared from optically active starting materials (obtained according to known methods for the separation of racemates).

The starting materials of formula II can, for example, be obtained by reacting a compound of formula V,

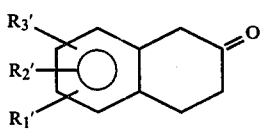

with a compound of formula VI,

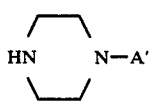

The reaction can be effected according to known methods. For example, the reaction can be effected in an inert solvent such as toluene, in the presence of a catalytic amount of p-toluene sulphonic acid with water separation, conveniently at the reflux temperature of the solvent or in the presence of a Lewis acid, e.g. titanium tetrachloride, conveniently at a temperature of from 20° to 100° C.

The resulting compounds of formula II can, without isolation be hydrogenated in situ to yield the compounds of formula Ia.

The reaction of a compound of formula V with a compound of formula VI can however lead directly to a compound of formula Ia, if the reaction is effected under reducing conditions. Suitable reducing agents include hydrogen in the presence of a catalytic amount of Raney-nickel, platinum or palladium on charcoal. The reaction may suitably be effected in a solvent, for example acetic acid, at room temperature.

The compounds of formulae III, IV, V and VI are either known or can be produced according to known methods.

In the following Examples all temperatures are in degrees Celsius.

EXAMPLE 1

1,2,3,4-Tetrahydro-6-methoxy-2-[4-(2-methylphenyl)-1-piperazinyl]-naphthalene 6 g of methoxy-2-tetralone together with 6 g of N-(o-tolyl)-piperazine are dissolved in 100 ml of toluene whilst warming, 300 mg of p-toluenesulphonic acid are added and the solution refluxed for 24 hours, whereby the water is separated using a Dean-Stark separator. The reaction mixture is then evaporated to dryness, 200 ml of dimethyl formamide and 300 mg of a 10% palladium on charcoal catalyst are added to the obtained 3,4-dihydro-6-methoxy-2-[4-(2-methylphenyl)-1-piperazinyl]-naphthalene, which is hydrogenated at normal pressure. When the take-up of hydrogen ceases the catalyst is filtered off, the solvent evaporated off and the residue chromatographed on Kieselgel with methylene chloride (methanol (99:1). The title compound is obtained as a compact residue. M.P. 286–288° [Hydrochloride salt form].

EXAMPLE 2

1,2,3,4-Tetrahydro-6-methoxy-2-[4-(2-methylphenyl)-1-piperazinyl]-naphthalene 3.6 g of 6-methoxy-2-tetralone are dissolved together with 3.9 g of N-(o-tolyl)-piperazine in 50 ml of acetic acid, 1 g of a 10% palladium on charcoal catalyst is added and hydrogenation effected. When the take-up of hydrogen ceases, the catalyst is filtered off, the solvent evaporated and the residue chromatographed on Kieselgel in manner analogous to that described in Example 1. The title compound is obtained as a compact residue. M.P. 286°–288° [Hydrochloride salt form].

EXAMPLE 3

1,2,3,4-Tetrahydro-6-hydroxy-2-[4-(2-methylphenyl)-1-piperazinyl]-naphthalene 10 g of 1,2,3,4-tetrahydro-6-methoxy-2-[4-(2-methylphenyl)-1-piperazinyl]-naphthalene are suspended in 200 ml of 47% aqueous hydrogen bromide and refluxed under a nitrogen atmosphere for 3 hours. The hydrogen bromide is finally evaporated off and the product which is in the form of the hydrobromide is converted to the free base form, with IN aqueous sodium bicarbonate solution/methylene chloride, and recrystallised from acetonitrile. The title compound is obtained as a compact residue. M.P. 177°–179°. Hydrochloride salt form: M.P. 304°–306°.

EXAMPLE 4

1,2,3,4-Tetrahydro-6-hydroxy-2-[4-(2-methoxyphenyl)-1-piperazinyl]-naphthalene 2.48 g of N,N-Di(2-chloroethyl)-2-methoxyaniline are dissolved together with 1.63 g of 2-amino-1,2,3,4-tetrahydro-6-hydroxynaphthalene in 100 ml of ethanol and finally refluxed for 20 hours. The solvent is evaporated off and the residue recrystallized from methanol/ether to yield the title compound. M.P. 282°–286° [Hydrochloride salt form].

EXAMPLE 5

1,2,3,4-Tetrahydro-6-acetoxy-2-[4-(2-methoxyphenyl)-1-piperazinyl]-naphthalene 170 mg of 1,2,3,4-tetrahydro-6-hydroxy-2-[4-(2-methoxyphenyl)-1-piperazinyl]-naphthalene are added to 2 ml of pyridine, 70 μl of acetic anhydride are added dropwise and the solution left to stand at room temperature for 3 hours. The reaction solution is finally evaporated to dryness, the residue taken up in ethyl acetate, washed with IN sodium carbonate solution, dried and evaporated to dryness. The raw title product so obtained is converted to the hydrochloride salt form and recrystallized from methanol/ether. M.P. 249°–253° [Hydrochloride salt form].

EXAMPLE 6

(+)- and (−)-1,2,3,4-Tetrahydro-6-hydroxy-2-[4-(2-methylphenyl)-1-piperazinyl]-naphthalene (a) (+)- and (−)-2-Amino-1,2,3,4-tetrahydro-6-methoxynaphthalene 47 of D-(−)-mandelic acid, dissolved in 650 ml of methanol, are added dropwise, whilst stirring, to a solution of 55 g of 2-amino-1,2,3,4-tetrahydro-6-methoxynaphthalene in 650 ml of methanol. The reaction solution so obtained is left to stand for 3 hours at room temperature, the precipitated crystals filtered off, washed with ether and dried. The (−)-mandelic acid salt thus obtained, is recrystallised from hot methanol and the procedure repeated until, at any given time a test showed that the optical rotation of the amine set free from the mandelic acid salt by extraction with IN sodium carbonate solution/methylene chloride is constant. The (+)-antipode of the title compound thus obtained is converted to the hydrochloride and recrystallised from methanol. M.P. 262°–264°. $[\alpha]_D^{20} = +77.6°$ (C=1 in methanol). [Hydrochloride salt form].

The (−)-antipode of the title compound is obtained in manner analogous to the aforementioned method and employing (+)-mandelic acid in place of (−)-mandelic acid. The (−)-antipode is converted to the hydrochloride salt form and recrystallised from methanol. M.P. 263°–265°. $[\alpha]_D^{20} = -78.6°$ (C=1 in methanol) [Hydrochloride salt form].

(b) (+)- and (−)-2-amino-1,2,3,4-tetrahydro-6-hydroxynaphthalene

The aforementioned (+)-2-amino-1,2,3,4-tetrahydro-6-methoxynaphthalene is converted into the corresponding hydroxy compound by ether cleavage in manner analogous to that described in process variant (b), converted to the hydrochloride salt form and finally recrystallized from methanol to yield the (+)-antipode of the title compound. M.P. 276°-278°. $[\alpha]_D^{20} = +80.5°$ (C=1 in methanol) [Hydrochloride salt form].

The (−)-antipode of the title compound is obtained in manner analogous to the above process, but employing (−)-2-amino-1,2,3,4-tetrahydro-6-methoxynaphthalene, M.P. 276°-278°. $[\alpha]_D^{20} = -83.0$ (C=1 in methanol). [Hydrochloride salt form].

(c) (+)- and (−)-1,2,3,4-tetrahydro-6-hydroxy-2-[4-(2-methylphenyl)-1-piperazinyl]-naphathalene The (+)-antipode of the title compound can be obtained by condensing (+)-2-amino-1,2,3,4-tetrahydro-6-hydroxynaphthalene with N,N-di(2-chloroethyl)-2-methylaniline according to process variant (c) and finally recrystallizing the product from acetonitrile. M.P. 147°-149°. $[\alpha]_D^{20} = +49.7°$ (C=1 in methanol)

In analogous manner, the (−) antipode of the title compound can be obtained starting from (−)-2-amino-1,2,3,4-tetrahydro-6-hydroxynaphthalene. M.P. 146°-148° $[\alpha]_D^{20} = -50.3$ (C=1 in methanol).

The compounds set out in Tables I and II can be obtained in manner analogous to the methods described in Examples 1, 2 and 3 using appropriate starting materials in approximately equivalent amounts.

TABLE I

Compounds of formula

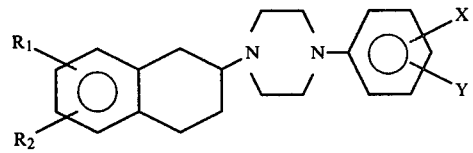

| Ex. No. | R₁ | R₂ | X | Y | Analogy Ex. | M.P. | Salt Form |
|---|---|---|---|---|---|---|---|
| 7 | 6-CH₃O | 7-CH₃O | 2-CH₃ | H | 1 | 277–280° | (Dihydrochloride) |
| 8 | 6-OH | 7-OH | 2-CH₃ | H | 3 | 305–308° | (Dihydrochloride) |
| 9 | 6-OH | H | 2-Cl | H | 4 | 303–305° | (Hydrochloride) |
| 10 | 6-OH | H | 4-CH₃O | H | 4 | 297–301° | (Dihydrochloride) |
| 11 | 5-CH₃O | H | 2-CH₃ | H | 4 | 281–282° | (Hydrochloride) |
| 12 | 5-OH | H | 2-CH₃ | H | 3 | 333–336° | (Hydrochloride) |
| 13 | 6-CH₃O | H | 4-CH₃O | H | 1 | 244–246° | (Dihydrochloride) |
| 14 | 6-OH | H | 4-OH | H | 3 | 302–305° | (Dihydrochloride) |
| 15 | 7-CH₃O | H | 2-CH₃ | H | 1 | 270–271° | (Hydrochloride) |
| 16 | 7-OH | H | 2-CH₃ | H | 3 | 277–279° | (Dihydrochloride) |
| 17 | 5-CH₃O | 8-CH₃O | 2-CH₃O | H | 1 | 291–293° | (Hydrochloride) |
| 18 | 6-OH | H | H | H | 3 | 324–326° | (Dihydrochloride) |
| 19 | 6-CH₃O | H | 3-CF₃ | H | 1 | 254–255° | (Dihydrochloride) |
| 20 | 6-OH | H | 3-CF₃ | H | 3 | 223–224° | (Dihydrochloride) |
| 21 | 6-OH | H | 3,4-O—CH₂—O | | 4 | 298–300° | (Dihydrochloride) |
| 22 | 6-CH₃O | H | 3-CH₃O | 4-CH₃O | 4 | 238–240° | (Dihydrochloride) |
| 23 | 6-OH | H | 3-CH₃O | 4-CH₃O | 4 | 275–278° | (Dihydrochloride) |
| 24 | 6-OH | H | 2-CH₃ | 6-CH₃ | 3 | 306–308° | (Hydrochloride) |
| 25 | 6-CH₃O | H | 4-Cl | H | 4 | 257–259° | (Dihydrochloride) |
| 26 | 6-OH | H | 4-Cl | H | 4 | 310–312° | (Hydrochloride) |
| 27 | 6-OH | H | 2-C₂H₅O | H | 4 | 304–307° | (Hydrochloride) |
| 28 | 6-OH | H | 2-Cl | 5-CH₃O | 4 | 294–296° | (Hydrochloride) |
| 29 | 6-OH | H | 2-Cl | 5-OH | 3 | 301–304° | (Hydrochloride) |
| 30 | 6-OH | H | 2-CH₃O | 5-CH₃O | 4 | 269–271° | (Dihydrochloride) |
| 31 | 6-OH | H | 2-CH₃O | 5-OH | 3 | 285–287° | (Hydrochloride) |
| 32 | 6-OH | H | 2-CH₃O | 4-CH₃O | 4 | 282–286° | (Dihydrochloride) |
| 33 | 6-OH | H | 2-CH₃O | 4-OH | 3 | 271–275° | (Dihydrochloride) |

TABLE II

Compounds of formula

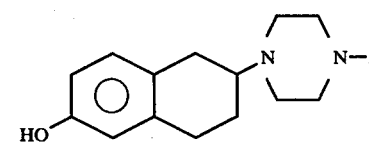

| Ex. No. | A | Analogy Ex. | M.P. | Salt Form |
|---|---|---|---|---|
| 34 | 1-Naphthyl | 3 | 302–306° | (Dihydrochloride) |
| 35 | 2-Pyrimidinyl | 4 | 270–273° | (Dihydrochloride) |
| 36 | 2-Pyridyl | 4 | 264–266° | (Dihydrochloride) |
| 37 | 2-Imidazolin-2-yl | 3 | | (Dihydrochloride) |
| 38 | 2-Thiazolyl | 3 | 244–247° | (Dihydrochloride) |

The following compounds can be prepared in manner analogous to those described in one or more of the preceding Examples.

| Ex. No. | R₁ | R₂ | R₃ | A |
|---|---|---|---|---|
| 39 | 6-C₇H₁₅CO₂ | H | H | 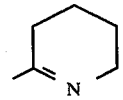 |

-continued

| Ex. No. | R₁ | R₂ | R₃ | A |
|---|---|---|---|---|
| 40 | 7-OCH₃ | C₃H₇ at 6-position of phenyl-CO₂ | H | tetrahydro-oxazine ring |
| 41 | F at 8-position, Br, phenyl-CO₂ | H | H | CF₃-phenyl-SC₂H₅ |
| 42 | 6-OCH₃ | 7-methylenedioxy-phenyl-CO₂ | 8-OCH₃ | phenyl-CH₃ |
| 43 | 5-C₇H₁₅COO | H | H | tetrahydro-N=C-NH, OCH₃-phenyl |
| 44 | 5-OCH₃ | 6-OCH₃ | 8-methylenedioxy-phenyl-COO | |
| 45 | 6-OCH₃ | H | H | C₂H₅COS, phenyl, C₂H₅COS |

The compounds of formula I are useful because they possess pharmacological activity in animals. In particular, the compounds are useful as anti-hypertensive agents for the treatment of hypertension as indicated in standard tests, for example as demonstrated by dopamine receptor stimulation which produces an increase in mesenteric blood flow in the anaesthetised dog on i.v. administration of from 0.1 to 15 mg/kg of animal body weight of the compounds.

For this use, the dosage will of course vary depending on the compound employed, mode of administration and treatment desired. However, in general, satisfactory results are obtained when administered at a daily dosage of from about 0.3 to about 15 mg/kg of animal body weight conveniently given in divided doses 2 to 4 times a day or in sustained release form. For the larger mammal, the total daily dosage is in the range of from about 15 to about 1000 mg and dosage forms suitable for oral administration comprise from about 4 to about 500 mg of the compounds admixed with a solid or liquid pharmaceutical carrier or diluent.

The compounds of formula I may be administered in pharmaceutically acceptable acid addition salt forms. Such acid addition salt forms exhibit the same order of activity as the free base forms and are readily prepared in conventional manner. The present invention also provides a pharmaceutical composition comprising a compound of formula I, in free base form or in pharmaceutically acceptable acid addition salt form, in association with a pharmaceutically acceptable diluent or carrier. Such compositions may be formulated in conventional manner and may be in the form of, for example, a solution or a capsule.

Suitable acids for salt formation include hydrochloric and maleic acids.

In one group of compounds, $R_1$ is hydroxy, akloxy of 1 to 4 carbon atoms, alkanoyloxy of 1 to 4 carbon atoms or benzoyloxy, each of $R_2$ and $R_3$ is independently hydrogen, hydroxy, alkoxy of 1 to 4 carbon atoms, alkanoyloxy of 1 to 4 carbon atoms or benzoyloxy, or $R_1$ and $R_2$ when bonded to adjacent carbon atoms can together be a methylenedioxy group, A is a

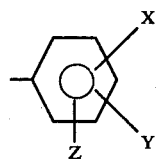

group wherein each of X, Y and Z is independently hydrogen, hydroxy, alkyl of 1 to 4 carbon atoms, alkoxy of 1 to 4 carbon atoms, alkanoyloxy of 1 to 4 carbon atoms, benzoyloxy, fluorine, chlorine or $CF_3$, or X and Y when bonded to adjacent carbon atoms can together be a methylenedioxy group.

In a second group of compounds, $R_1$ is hydroxy, alkoxy of 1 to 4 carbon atoms, alkanoyloxy of 1 to 20 carbon atoms or a

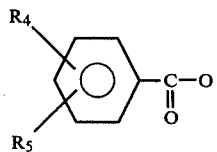

group, wherein each of $R_4$ and $R_5$ is independently hydrogen, fluorine, chlorine, bromine, iodine, alkyl of 1 to 4 carbon atoms or alkoxy of 1 to 4 carbon atoms.

I claim:
1. A compound of formula

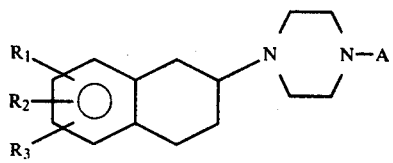

wherein $R_1$ is hydroxy, alkoxy of 1 to 4 carbon atoms, alkanoyloxy of 1 to 20 carbon atoms or a

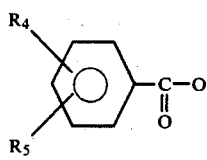

group,
wherein $R_4$ and $R_5$ may independently be hydrogen, fluorine, chlorine, bromine, iodine, alkyl of 1 to 4 carbon atoms or alkoxy of 1 to 4 carbon atoms or, when bonded to adjacent carbon atoms, $R_4$ and $R_5$ together may be a methylenedioxy group,
$R_2$ and $R_3$ may independently be hydrogen, hydroxy, alkoxy of 1 to 4 carbon atoms, alkanoyloxy of 1 to 20 carbon atoms or a

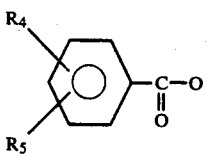

group, or when bonded to adjacent carbon atoms $R_1$ and $R_2$ together may be a methylenedioxy group,
A is
(a) a

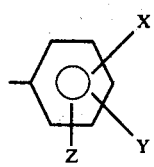

group,
wherein X, Y and Z may independently be hydrogen, hydroxy, alkyl of 1 to 4 carbon atoms, alkoxy of 1 to 4 carbon atoms, a

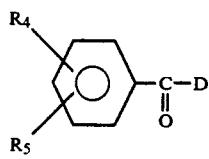

group, fluorine chlorine, bromine, iodine, $CF_3$, alkylthio of 1 to 4 carbon atoms or alkanoylthio of 1 to 20 carbon atoms, or when bonded to adjacent carbon atoms X and Y together may be methylenedioxy, D is O or S
(b) a

group,
(c) a five or six membered ring of formula

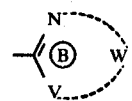

wherein
V is either divalent and signifies O, S, NH or $CH_2$ or trivalent and signifies N or CH,
W is a saturated or unsaturated alkylene chain of 2 or 3 carbon atoms
and ring B can contain 1, 2 or 3 double bonds, or a pharmaceutically acceptable acid addition salt thereof.

2. A method of treating hypertension, which comprises administering to an animal in need of such treatment, a therapeutically effective amount of a compound of claim 1.

3. A pharmaceutical composition comprising an antihypertensive effective amount of a compound of claim 1, in association with a pharmaceutically acceptable carrier or diluent.

4. A compound according to claim 1, in which $R_1$ is hydroxy, alkoxy of 1 to 4 carbon atoms, alkanoyloxy of 1 to 4 carbon atoms or benzoyloxy; $R_2$ and $R_3$ are each independently hydrogen, hydroxy, alkoxy of 1 to 4 carbon atoms, alkanoyloxy of 1 to 4 carbon atoms or benzoyloxy, or $R_1$ and $R_2$ together when bonded to adjacent carbon atoms is methylenedioxy, A is

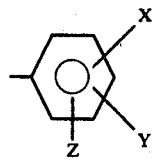

wherein X, Y and Z are each independently hydrogen, hydroxy, alkyl of 1 to 4 carbon atoms, alkoxy of 1 to 4 carbon atoms, benzoyloxy, flourine, chlorine or $CF_3$, or X and Y together when bonded to adjacent carbon atoms is methylenedioxy.

5. A compound according to claim 1 in which $R_1$ is hydroxy, alkoxy of 1 to 4 carbon atoms, alkanoyloxy of 1 to 20 carbon atoms or

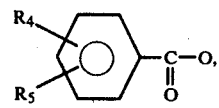

wherein $R_4$ and $R_5$ are each independently hydrogen, flourine, chlorine, bromine, iodine, alkyl of 1 to 4 carbon atoms or alkoxy of 1 to 4 carbon atoms.

6. The compound according to claim 1 which is 1,2,3,4-Tetrahydro-6-methoxy-2-[4-(2-methylphenyl)-1-piperazinyl]-naphthalene.

7. The compound according to claim 1 which is 1,2,3,4-Tetrahydro-6-hydroxy-2-[4-(2-methoxyphenyl)-1-piperazinyl]-naphthalene.

8. The compound according to claim 1 which is 1,2,3,4-Tetrahydro-6-acetoxy-2-[4-(2-methoxyphenyl)-1-piperazinyl]-naphthalene.

9. The compound according to claim 1 which is (+)-1,2,3,4-Tetrahydro-6-hydroxy-2-[4-(2-methylphenyl)-1-piperazinyl]-naphthalene.

10. The compound according to claim 1 which is (−)-1,2,3,4-Tetrahydro-6-hydroxy-2-[4-(2-methylphenyl)-1-piperazinyl]naphthalene.

11. The compound of claim 1 in which $R_3$ is hydrogen, A is

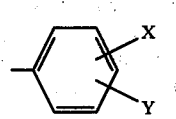

and $R_1$, $R_2$, X, and Y are 6-CH$_3$O, 7-CH$_3$O, 2-CH$_3$ and H respectively.

12. The compound of claim 1 in which $R_3$ is hydrogen, A is

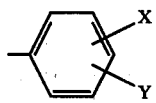

and $R_1$, $R_2$, X and Y are 6-OH, 7-OH, 2-CH$_3$ and H, respectively.

13. The compound of claim 1 in which $R_3$ is hydrogen, A is

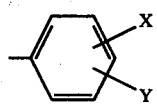

and $R_1$, $R_2$, X and Y are 6-OH, H, 2-Cl and H, respectively.

14. The compound of claim 1 in which $R_3$ is hydrogen, A is

and $R_1$, $R_2$, X and Y are 6-OH, H, 4-CH$_3$O and H, respectively.

15. The compound of claim 1 in which $R_3$ is hydrogen, A is

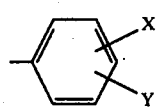

and $R_1$, $R_2$, X and Y are 5-CH$_3$O, H, 2-CH$_3$ and H, respectively.

16. The compound of claim 1 in which $R_3$ is hydrogen, A is

and $R_1$, $R_2$, X and Y are 5-OH, H, 2-CH$_3$ and H, respectively.

17. The compound of claim 1 in which $R_3$ is hydrogen, A is

and $R_1$, $R_2$, X and Y are 6-CH$_3$O, H, 4-CH$_3$O and H, respectively.

18. The compound of claim 1 in which $R_3$ is hydrogen, A is

and $R_1$, $R_2$, X and Y are 6-OH, H, 4-OH and H, respectively.

19. The compound of claim 1 in which $R_3$ is hydrogen, A is

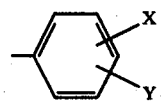

and $R_1$, $R_2$, X and Y are 7-CH$_3$O, H, 2-CH$_3$ and H, respectively.

20. The compound of claim 1 in which $R_3$ is hydrogen, A is

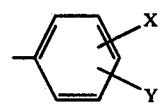

and $R_1$, $R_2$, X and Y are 7-OH, H, 2-CH$_3$ and H, respectively.

21. The compound of claim 1 in which $R_3$ is hydrogen, A is

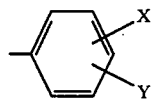

and $R_1$, $R_2$, X and Y are 5-$CH_3O$, 8-$CH_3O$, 2-$CH_3O$ and H, respectively.

22. The compound of claim 1 in which $R_3$ is hydrogen, A is

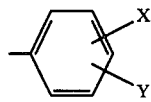

and $R_1$, $R_2$, X and Y are 6-OH, H, H and H, respectively.

23. The compound of claim 1 in which $R_3$ is hydrogen, A is

and $R_1$, $R_2$, X and Y are 6-$CH_3O$, H, 3-$CF_3$ and H, respectively.

24. The compound of claim 1 in which $R_3$ is hydrogen, A is

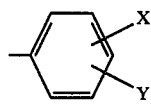

and $R_1$, $R_2$, X and Y are 6-OH, H, 3-$CF_3$ and H, respectively.

25. The compound of claim 1 in which $R_3$ is hydrogen, A is

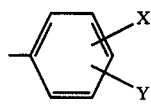

and $R_1$ is 6-OH, $R_2$ is H, and X and Y together is 3,4-O-$CH_2$-O.

26. The compound of claim 1 in which $R_3$ is hydrogen, A is

and $R_1$, $R_2$, X and Y are 6-$CH_3O$, H, 3-$CH_3O$ and 4-$CH_3O$, respectively.

27. The compound of claim 1 in which $R_3$ is hydrogen, A is

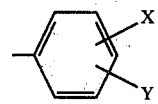

and $R_1$, $R_2$, X and Y are 6-OH, H, 3-$CH_3O$ and 4-$CH_3O$, respectively.

28. The compound of claim 1 in which $R_3$ is hydrogen, A is

and $R_1$, $R_2$, X and Y are 6OH, H, 2-$CH_3$ and 6-$CH_3$, respectively.

29. The compound of claim 1 in which $R_3$ is hydrogen, A is

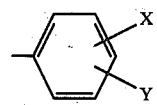

and $R_1$, $R_2$, X and Y are 6-$CH_3O$, H, 4-Cl and H, respectively.

30. The compound of claim 1 in which $R_3$ is hydrogen, A is

and $R_1$, $R_2$, X and Y are 6-OH, H, 4-Cl and H, respectively.

31. The compound of claim 1 in which $R_3$ is hydrogen, A is

and $R_1$, $R_2$, X and Y are 6-OH, H, 2-$C_2H_5O$ and H, respectively.

32. The compound of claim 1 in which $R_3$ is hydrogen, A is

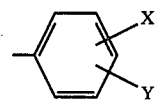

and $R_1$, $R_2$, X and Y are 6-OH, H, 2-Cl and 5-$CH_3O$, respectively.

33. The compound of claim 1 in which $R_3$ is hydrogen, A is

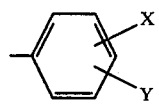

and $R_1$, $R_2$, X and Y are 6-OH, H, 2-Cl and 5-OH, respectively.

34. The compound of claim 1 in which $R_3$ is hydrogen, A is

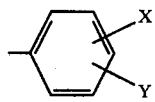

and $R_1$, $R_2$, X and Y are 6-OH, H, 2-$CH_3O$ and 5-$CH_3O$, respectively.

35. The compound of claim 1 in which $R_3$ is hydrogen, A is

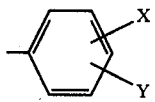

and $R_1$, $R_2$, X and Y are 6-OH, H, 2-$CH_3O$ and 5-OH, respectively.

36. The compound of claim 1 in which $R_3$ is hydrogen, A is and $R_1$, $R_2$, X and Y are 6-OH, H, 2-$CH_3O$ and 4-$CH_3O$, respectively.

37. The compound of claim 1 in which $R_3$ is hydrogen, A is

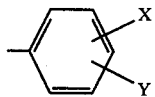

and $R_1$, $R_2$, X and Y are 6-OH, H, 2-$CH_3O$ and 4-OH, respectively.

38. The compound of claim 1 in which $R_1$ is 6-OH, $R_2$ and $R_3$ are each hydrogen and A is 1-naphthyl.

39. The compound of claim 1 in which $R_1$ is 6-OH, $R_2$ and $R_3$ are each hydrogen and A is 2-pyrimidinyl.

40. The compound of claim 1 in which $R_1$ is 6-OH, $R_2$ and $R_3$ are each hydrogen and A is 2-pyridyl.

41. The compound of claim 1 in which $R_1$ is 6-OH, $R_2$ and $R_3$ are each hydrogen and A is 2-imidazolin-2-yl.

42. The compound of claim 1 in which $R_1$ is 6-OH, $R_2$ and $R_3$ are each hydrogen and A is 2-thiazolyl.

43. 1,2,3,4-Tetrahydro-6-hydroxy-2-[4-(2-methylphenyl)-1-piperazinyl]-naphthalene.

* * * * *